United States Patent [19]

Garner et al.

[11] Patent Number: 5,387,526
[45] Date of Patent: Feb. 7, 1995

[54] COATED CAPILLARY TUBE FOR THE CONTROLLED RELEASE OF REAGENT

[75] Inventors: Harold R. Garner, Encinitas; Orenda F. Tuason; Larry S. Peranich, both of San Diego, all of Calif.

[73] Assignee: General Atomics, San Diego, Calif.

[21] Appl. No.: 30,445

[22] PCT Filed: Sep. 11, 1991

[86] PCT No.: PCT/US91/06567

§ 371 Date: Mar. 30, 1993

§ 102(e) Date: Mar. 30, 1993

Related U.S. Application Data

[63] Continuation-in-part of Ser. No. 581,521, Sep. 11, 1990, abandoned.

[51] Int. Cl.[6] .................................. G01N 21/03
[52] U.S. Cl. .................................. 436/169; 422/56; 422/57; 422/82.09; 422/100; 435/288; 435/291; 435/6; 436/518; 436/524; 436/527; 436/94; 436/810; 427/2.13; 427/8; 427/164; 356/244
[58] Field of Search .................... 422/55–58, 422/82.05, 82.08, 99, 100, 102; 435/288, 291, 6; 436/527, 169, 810, 518, 524, 94; 356/244, 246; 427/2, 8, 162, 164

[56] References Cited

U.S. PATENT DOCUMENTS

| | | | |
|---|---|---|---|
| 3,434,859 | 3/1969 | Benjamin | 117/17 |
| 3,918,908 | 11/1975 | Moyer et al. | 23/230 |
| 4,308,029 | 12/1981 | Siggaard-Andersen | 23/230 |
| 4,482,636 | 11/1984 | Mochida et al. | 436/518 |
| 4,495,151 | 1/1985 | Ohyama et al. | 422/102 |
| 4,533,629 | 8/1985 | Litman et al. | 435/7 |
| 4,608,231 | 8/1986 | Witty et al. | 422/61 |
| 4,865,813 | 9/1989 | Leon | 422/101 |
| 4,921,788 | 5/1990 | Deutsch | 435/6 |
| 4,960,566 | 10/1990 | Mochida | 422/65 |
| 4,991,958 | 2/1991 | Garner | 356/244 |
| 5,009,998 | 4/1991 | Chow et al. | 435/7.92 |
| 5,073,484 | 12/1991 | Swanson et al. | 435/7.92 |

FOREIGN PATENT DOCUMENTS 2005831 4/1979 United Kingdom.

OTHER PUBLICATIONS

Fisher Scientific Product Catalog, p. 1141 (1986).
Fritz, J. S. et al., *Quantitative Analytical Chemistry*, 4th Edition, Boston, Mass. pp. 102–103 (1979).
Chandler, et al., Device and method for detecting antigens, antibodies, and haptens, CA 111(19):172317k (1989).
Gist–Brocades, N. V., Device for chemical and microbiological analyses, CA 90(19):148114u (1981).

*Primary Examiner*—James C. Housel
*Assistant Examiner*—David Kelly
*Attorney, Agent, or Firm*—Fitch, Even, Tabin & Flannery

[57] ABSTRACT

A hollow, elongated, micropipette, which is specially adapted for use in spectrometers and which has an inner wall on which a coating containing a reagent has been deposited, is provided. The reagent is selected from among those that interact with one or more compounds in a sample solution, which is introduced into the micropipette, in order to permit the compounds to be detected by virtue of light absorption or emission by the complexes formed upon interaction of the reagent with the compound of interest in the sample.

Upon introduction of the sample solution into the micropipette, a sufficient amount of the reagent in the coating dissolves in the solution and reacts, either directly or indirectly with a compound or compounds of interest in the solution to render such compound detectable and to permit quantification of the concentration of the compound in the sample. The resulting solution is held in the micropipette for analysis of the light absorption or light emission characteristics of the solution to determine the composition of the solution or the concentration of a particular constituent of the solution.

In preferred embodiments, the coating on the inner surface of the micropipette includes a binding agent or adhesive that delays, preferably for about 5 to 15 sec, the dissolution of the reagent in the solution.

11 Claims, 2 Drawing Sheets

COATED CAPILLARY TUBE FOR THE CONTROLLED RELEASE OF REAGENT

RELATED APPLICATIONS

This application is a continuation-in-part of U.S. patent application Ser. No. 07/581,521, to Garner et al., filed Sep. 11, 1990, "COATED CAPILLARY TUBE" now abandoned. This application is related to U.S. Pat. No. 4,991,958 to Garner, filed Jul. 10, 1989, "MICROPIPETTE ADAPTOR FOR SPECTROPHOTOMETERS" and to U.S. patent application Ser. No. 07/433,752, to Garner, filed Nov. 9, 1989, "MICROPIPETTE ADAPTOR FOR SPECTROFLUORIMETERS". The subject matter of U.S. patent application Nos. 07/581,521 and 07/433,752 and U.S. Pat. No. 4,991,958 is incorporated herein in its entirety by reference thereto.

FIELD OF THE INVENTION

The present invention relates generally to devices that are useful for spectrometric analysis of the components of solutions. More particularly, the present invention relates to containers or tubes that are mountable in a spectrometer and that have interior surfaces coated with compositions that include reagents used for the spectrometric analysis of the components of solutions that have been introduced into the tubes in order to detect, identify and measure the concentrations of such components in the solutions. The invention also relates to methods for preparing the coated tubes and to methods for using the coated tubes. The present invention is particularly, though not exclusively, useful for rapidly and quantitatively detecting and identifying particular compounds in a relatively small amount of a solution.

BACKGROUND OF THE INVENTION

Spectroscopy is used in a variety of fields to determine the compositions of solutions by identifying and measuring the wavelengths and intensity of electromagnetic radiation absorbed or emitted by compounds in the solution. Spectroscopy is particularly useful for identifying, characterizing and quantifying compounds that absorb in the ultraviolet (U.V) or visible portion of the spectrum because many biologically important macromolecules, including biopolymers, such as DNA, RNA, proteins and carbohydrates, absorb energy in at least one region of the spectrum of U.V. or visible portion of the electromagnetic spectrum. Under appropriate conditions it is possible, using spectrometry to detect, identify and measure the concentration of such compounds in solution.

Upon exposure of a solution to incident light that includes wavelengths that have energy that matches the difference between two allowed states of compounds in the solution, photons of the particular wavelength are absorbed so that the component wavelengths of the transmitted light differ from those of the incident light. Following absorption, the electrons in the compounds revert ground state by loss of energy to collisions and other heat generating interactions. For some compounds, however, particularly those that have conjugated electrons, reversion to ground state is slower and includes the emission of photons. Depending upon the nature of the excited state the emission may result in fluorescence. Fluorescent emissions have a lower energy level than the incident absorbed light and may be detected with high sensitivity by a photodetector, as long the incident light does not interfere with the emitted light. Typically, in fluorescence spectrometers the photodetector is placed at an angle, usually at right angles, to the incident light. When absorption or emission is in the U.V and visible region of the spectrum, such transitions are particularly suitable for measurement by photometric methods, including absorbance spectrophotometry and fluorescence spectrophotometry. In practice, a sample of a solution containing a compound, such as a biopolymer, is introduced into a cuvette, a container which is transparent to the wavelength absorbed by the compound of interest, and the cuvette is placed into a spectrometer, such as a spectrophotometer or spectrofluorimeter. Absorbance spectrophotometry and fluorescence spectrometry (spectrofluorimetry) involve the measurement of electronic transitions of compounds, either by absorption or emission or electromagnetic radiation, and permit the detection, characterization and quantification of such compounds in solutions. The energy at which absorption occurs is a function of the electron, vibrational and rotational energy levels of the compounds in the solution.

In order to enhance or alter the light absorption or light emission characteristics of a particular compound or to detect a particular constituent of a solution or mixture of compounds, it is sometimes necessary to add an appropriate reagent, which specifically interacts with the chemical or compound of interest, to the solution prior to analysis. The reagent specifically interacts with the chemical or compound of interest to form a complex or other product that has different absorption or emission properties than either the compound or reagent alone. The reagent is selected to combine with a particular compound or precursor of the compound that is present in the solution to form a complex that has enhanced light absorption or light emission characteristics compared to the compound in the absence of the reagent and that can be detected using an absorbance spectrophotometer, fluorescence spectrometer, or other photometric instrument, or even observed with the naked eye. For example, highly fluorescent compounds are relatively rare and may be used as reagents for tagging non-fluorescent or weakly fluorescent compounds. A fluorescent compound can be bound or otherwise complexed with a non-fluorescent compounds and thereby provide a means for detecting, identifying and quantifying such non-fluorescent compounds.

Absorbance is directly proportional to concentration so that the concentration of particular compounds may be determined from absorbance measurements. Fluorescence is directly proportional to concentration only in dilute solutions. It is generally a function of several variables, including incident intensity and the particular instrument used. Concentrations of fluorescent compounds may be measured using fluorescent spectrometry by preparing a standard curve.

In particular, in studying samples of body fluids or solutions of biopolymers that contain compounds, such as DNA, RNA, proteins and carbohydrates, detection and quantification of the concentration of the compound is improved by first contacting the solution with a reagent such as a dye or fluorescent compound, that reacts with a particular compound in solution and alters or enhances the absorbance or emission of electromagnetic radiation by the compound.

In order to conduct typical spectrophotometric and spectrofluorimetric and other photometric assays for macromolecules, a specific reagent is added to a sample solution that contains the compound of interest. The reagent interacts with the macromolecule to form a complex that is directly or indirectly detectable a characteristic absorbance or fluorescence profile. The reagent forms a complex or other product that absorbs, emits or produces electromagnetic radiation of a specific or particular wavelength that can be used to detect, identify or quantify the concentration of the compound of interest in the sample solution. Such reagents include, dyes, such as Hoechst dye, (2-(2-(4-hydroxyphenol)-6-benzymidazoyl-6(1-methyl-4-piperazyl)benzimidazole), which interacts with DNA to form a complex that has increased fluorescence, and various dyes, such as Coomassie blue, that bind to proteins and result in colored products that absorb strongly in the visible portion of the spectrum. The concentration of the macromolecule, such as DNA or protein, may be determined by measuring the absorbance or emission at selected absorbance or fluorescence maxima.

Since detection of the particular compound requires modification of the compound, the sample may be discarded after the measurement is made. Since the amount of sample that is available for study is often very limited, it is desirable to use as little of the sample as possible for spectroscopic analysis. The amount of sample that is used, however, is constrained by the limits of detection of the system. Generally, as the size of the cuvette is decreased, the amount of sample is reduced, which in turn decreases the size of the signal produced upon exposure of the sample to light emitted by the spectrophotometer, thereby decreasing the sensitivity and accuracy of the measurement. If the solution is introduced into a standard cuvette, which is about 12.5 mm $\times$ 12.5 mm and which must be completely filled for accurate measurements, and if the limits of detection are in the 1–10 $\mu g/ml$ range, then a substantial portion of the available sample may be depleted by spectrometric analysis.

U.S. Pat. No. 4,991,958 and U.S. patent application Ser. No. 07/433,752 to Garner, which have herein been incorporated in their entirety by reference thereto, describe adaptors for spectrometric analysis that are designed to properly focus light onto a sample held in a micropipette that is mounted in the adaptor in a spectrophotometer and in a fluorescence spectrometer, respectively. By virtue of the design, the adaptors provide means for spectrometric measurements of small samples. Each adaptor is designed to focus light from the spectrometer light source along the axis of the micropipette and to refocus light emitted from or through the pipette so that it is received by the detector. U.S. Pat. No. 4,991,958 and U.S. patent application No. 07/433,752 to Garner, however, provide little guidance regarding the optimal design of micropipettes for use in the adaptors.

In addition, since many spectrometric assays for macromolecules rely on the addition of regents to render the macromolecule detectable, the reagents must be premixed with the sample solution to form detectable products. Such pre-mixing of reagent and the sample creates other technical complications, including exposing the analysts to physically harmful chemicals, such as ethidium bromide. Also, typically the reagents are added and mixed in cuvettes. Because cuvettes are quartz or glass or other suitable material that is transparent to a particular range of wavelengths, and, because they are optical components of the spectrometer, they must be engineered to fairly exacting specifications. Consequently cuvettes, generally, are not disposable. Such reusable cuvettes or other containers may become contaminated and hence unsuitable for subsequent use. Additionally, such reuse can result in contamination of the sample.

Thus, there a need to provide a receptacle that can hold a relatively small sample for analysis within a spectrometer. In addition, in order to facilitate spectroscopic analysis, there is a need to provide a means by which a reagent can easily and safely be mixed with the relatively small amount of sample that is held within the micropipette and to provide means for accurately detecting and quantifying the concentrations of particular compounds that are present in samples in relatively low concentrations and in relatively small volumes.

Therefore, it is an object of the present invention to provide a micropipette that is designed to hold a relatively small sample of the liquid in a spectrometer.

It is a further object of the present invention to provide a micropipette mountable in a spectrophotometer that holds a liquid sample in the spectrometer and that includes means for safely and easily mixing a reagent with the sample solution.

Another object of the present invention is to provide a micropipette for holding a liquid sample in a spectrometer in which a reagent can be pre-mixed with a compound in solution in a reproducible and standardized procedure.

It is another object is to provide a disposable micropipette for holding a sample solution in a spectrometer. A further object is to provide a micropipette for holding a liquid sample in a spectrometer which reduces the likelihood of contamination of the liquid held in the micropipette. Another object is to provide a micropipette, for holding a sample solution in a spectrometer, that is relatively easy to use and comparatively cost-effective to manufacture.

SUMMARY OF THE INVENTION

A hollow container, such as a capillary tube or micropipette, that has an interior lumen uniformly coated with a composition that includes at least one reagent that forms detectable complexes with macromolecules, biopolymers and other compounds is provided. The container has an outer wall and an inner wall that defines the lumen of the container. The walls of the container may have circular or non-circular, such as rectangular, cross-sections and must be transparent to at least a portion of the electromagnetic spectrum. In embodiments in which the container is a tube that is mountable in a spectrophotometer, the inner diameter, outer diameter, and wall thickness of the tube, which must serve as an optical component of a spectrometer, must be uniform along its length (longitudinally), in the radial or circular direction (azimuthally) and must be uniform among tube.

The coating composition must be applied uniformly along the inside walls of the tube or container. The coating composition includes the reagent at a concentration such that, upon introduction of a solution containing a compound or compounds that interact with the reagent, sufficient reagent dissolves in the solution that is introduced into the tube to at least permit detection of compounds in the solution and may permit quantification of compounds in the solution.

In preferred embodiments, the container is a tube, particularly a capillary tube or micropipette, that has an inside diameter (lumen diameter) of approximately one-half (0.5) mm. Accordingly, the lumen of the tube has a relatively small volume and can be filled with small amount of a sample solution for spectrometric analysis of the constituent compounds in the sample solution.

The lumen of the tube is coated with a coating composition that contains the reagent that interacts with compounds in the sample solution resulting in detectable complexes or other detectable compounds. The reagent is selected on the basis of its ability to combine with compounds in the solution and to form a solution that has enhanced light emission or light absorption characteristics, whereby the compounds may be detected and quantified by spectrometric analysis. More particularly, the solution can be analyzed by a spectrometric technique that is appropriate for the particular type of compound and reagent. For example, the solution formed within the micropipette by the reagent and the compound in solution may be analyzed by mounting the tube within a spectrophotometer or fluorescence spectrometer. Then, the light absorption or light emission characteristics, respectively, of the solution may be measured. Alternatively, the reagent may be a dye which forms a colored solution with the compounds in the sample solution in the micropipette. It may be possible to identify the compound in the solution by visually observing the color of the solution. Also, the solution may be analyzed using infrared or laser waveform analysis techniques.

In preferred embodiments, the coating composition includes a binding agent or adhesive that serves to decrease the rate that the reagent in the coating dissolves in the sample solution when the solution is introduced into the tube. The binding agent or adhesive is a viscous mixture prepared by mixing one or more simple sugars, polysaccharides, gelatin or other viscous substance that is inert with respect to the selected reagent or reagents and the sample solution. The binding agent or adhesive is selected on the basis of its ability to act to delay the immediate dissolution of the reagent which is part of the coating composition when the sample solution is introduced into the tube. Including a binding agent or agents in the coating composition provides a means for uniformly distributing the reagent in the sample solution.

The coating may be applied to the surface by any means known to those of skill in the art. The particular method used to deposit the composition is in part dictated by the characteristics of the particular reagent. For example, reagents, such as ethidium bromide and Hoechst dye, may be mixed with water to form a reagent solution. The reagent solution may then be introduced into the lumen of the micropipette and evaporated to deposit the reagent on the inner wall of the micropipette in the form of a dry residue which adheres to the inner wall of the micropipette. Alternatively, the reagent, again in liquid solution, may be sprayed onto the inner wall of the micropipette through a needle-like spraying device which can be inserted into the lumen of the micropipette.

In preferred embodiments, the coating composition is introduced into the tube as a coating mixture or solution that is dried by evaporation to form the coating composition. The reagent in the coating is reversibly bound to the walls of the tube so that, upon introduction of the solution containing compounds with which the reagent interacts, the reagent forms a solution or suspension in the tube. In order to coat the inner walls of the tubes, a composition containing the binding agent or adhesive and one or more reagents that interact with compounds in the samples of interest is deposited substantially uniformly on the inner wall of the lumen of the tube. If desired, a second composition containing additional reagents that interact with other compounds in the sample may be deposited on predetermined portions of the inner wall. The concentration of the second reagent may be different from that of the first reagent. To these ends, the first and second reagents can be deposited on the inner wall of the micropipette in annular "pads" for respectively reacting with compounds in the sample solution. Further, additional compositions containing additional reagents may be deposited on the inner wall in additional "pads" to react with additional compounds in the sample solution. Alternatively, a single coating mixture containing a plurality of reagents may be prepared and uniformly coated on the inner walls of the tube.

In embodiments in which multiple reagents are deposited on the wall in annular pads, the reagent may be irreversibly or substantially irreversibly bound to the wall and does not dissolve when the sample solution is introduced into the lumen 26. In such embodiments, compounds in solution bind to the reagent that is attached to the wall forming distinguishable rings along the wall.

In other embodiments, an adhesive or binder layer is first deposited onto the inner wall of the micropipette. Then, a reagent in dry powder or viscous liquid form is introduced into the lumen, and the reagent sticks to the adhesive layer. Alternatively, in preferred embodiments, the adhesive layer is pre-mixed with the coating reagent and then the mixture is uniformly deposited on the inner surface of the tube.

DETAILED DESCRIPTION OF THE INVENTION

Definitions

Unless defined otherwise, all technical and scientific terms used herein have the same meaning as is commonly understood by one of skill in the art. All publications mentioned herein are incorporated by reference thereto. All U.S. patents mentioned herein are incorporated in their entirety by reference thereto.

As used herein, a photometer is an instrument that measures light output or luminescence.

As used herein, spectrometry is the procedure of observing and measuring electromagnetic emissions. A spectrometer is an instrument for measuring electromagnetic emissions. A spectrophotometer is an instrument for measuring the intensity of light of a particular wavelength that is transmitted by a substance or a solution, thereby providing a quantitative measurement of the concentration of a compound in solution. Spectrofluorimetry refers to the method of measuring the intensity and quality of fluorescence. A spectrofluorimeter is a spectrometer that is designed for measuring fluorescence.

As used herein, spectrometric analysis refers to analysis conducted using spectrometers, which measure absorbance of electromagnetic energy, spectrophotometers, which measure absorbance of visible or U.V. energy; fluorescence spectrometers, which measure emitted electromagnetic energy, and other photometers or devices known to those of skill in the art that are suitable for measuring absorption or emission of electromagnetic energy. Such devices may be designed to detect such absorption or emission of any type electromagnetic energy and are not limited to those that detect absorption or emission of U.V. or visible wavelengths. In preferred embodiments, spectrophotometers and fluorescence spectrometers that measure adsorbed and emitted electromagnetic energy, respectively, in the U.V and visible range are employed.

As used herein, capillary tube refers to a tube engineered from glass, quartz or other suitable material, that holds a relatively small volume and is suitable for mounting in an absorbance spectrophotometer, fluorescence spectrometer or other device in which the absorption or emission of light by compounds in solutions that are introduced into the capillary tube may be measured. Since the capillary tube is intended to be used as a component of a spectrometer or other such device, the optical properties of the tube must be sufficiently uniform so that optical properties of the components in solutions in the tube can be accurately and reliably detected and quantified. For example, the material from which the tube is fabricated must be transparent to the wavelength of interest, such as quartz for U.V. absorption or emission, and the tube must have uniform inner and outer diameters. Further, the tube may be engineered to be of any shape, including, circular, rectangular or any other shape that is suitable for conducting the necessary optical measurements.

As used herein, capillary tube does not necessarily imply that the tube must be filled by virtue of capillary action, but is used to denote the small cross sectional area. Any other term, such as micropipette, that one of skill in the art would recognize as referring to such a device may be used interchangeably with capillary tube. In preferred embodiments, the capillary tube is a micropipette that has an inside diameter (lumen diameter) of approximately one-half (0.5) mm.

As used herein, reversibly bound refers to the preferred manner in which the reagent is bound to the inner walls of the tube. The reagent is selected and deposited on the inner wall of the tube, such that, upon introduction of the sample into the tube, a substantial portion of the reagent does not remain attached to the wall, but dissolves or is suspended in the solution. In certain embodiments, however, the reagent is bound to the tube in annular "pads" and, upon introduction of the sample solution, a substantial portion of the reagent does not dissolve or detach from the wall.

As used herein, to quantitatively bind a compound or compounds, means to bind substantially all of the compound or compounds in a sample, and to thereby permit the amount or concentration of the compound to be determined.

As used herein, a binding agent refers to any compound or mixture of compounds that, when mixed with a reagent for detecting a compound of interest, and applied to the inner wall of a capillary tube used in spectrometric analysis, delays the dissolution of the reagent in coating into the solution. The delay is sufficient to permit uniform dissolution of the reagent in the coating in the sample solution and is preferably about 5 to 15 sec following introduction of the sample solution into the tube.

As used herein, a solution includes mixtures that are true solutions or suspensions of finely divided particles as long as the light diffraction resulting from any suspended particles does not interfere with detection of absorbed or emitted electromagnetic radiation.

Physical characteristics of the coated tubes and introduction of such tubes into spectrometers.

The coated tubes must be manufactured from material that is transparent to the incident light in the spectrometer and to the resulting light that passes through the tube or that is emitted by the complexes in the sample solution in the tube. For example, for measurements that include incident or emitted light in the U.V. range the tubes may be manufactured from quartz.

The tubes may be of any diameter or shape that is suitable for mounting in a spectrometer or other instrument used for analysis of the contents of the tubes. In preferred embodiments the tubes are micropipettes or capillary tubes in form and size and are especially adapted for use with an adaptor, such as that described by U.S. Pat. No. 4,991,958 to Garner. The inner diameter, outer diameter and wall thickness must be uniform along the length of capillary (longitudinally) and in the radial direction (azimuthally) and must be uniform among capillaries so that the tubes may serve as optical components of a spectrometer or other instrument in which the solution in the tube is analyzed. The tubes must be sufficiently uniform among each of the dimensions to provide reliable and accurate measurements.

Figure 1:
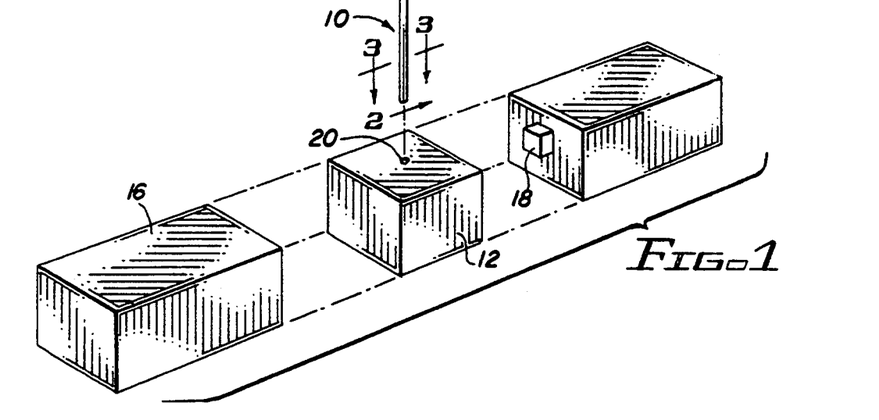
FIG. 1 is a perspective view of the coated micropipette, shown in an exploded relationship with a spectrometer.

Preferred embodiments are depicted in the Figures. In FIG. 1, a hollow micropipette or capillary tube, generally designated 10, is shown in an exploded relationship with an adapter 12, which is positionable in a spectrometer that includes a source 16 of light and a light detector 18. While source 16 and detector 18 are shown in FIG. 1 as boxes, it is to be understood that source 16 and detector 18 are any well-known light emission and detection devices, respectively, which are appropriate for use in a spectrometer or other such instrument known to those of skill in the art. As shown, micropipette 10 can be inserted into slot 20 of adapter 12. Adapter 12 can thus hold micropipette 10 within slot 20 between light source 16 and light detector 18 for spectrometric analysis of the sample solution (not shown in FIG. 1) in the lumen of micropipette 10. The spectrometer which includes source 16 and detector 18 may be a spectrophotometer, as shown in FIG. 1, or rearranged to establish a fluorescence spectrometer (not shown) for respectively analyzing the light emission or light absorption characteristics of the compounds in the sample solution in micropipette 10.

Figure 2A:
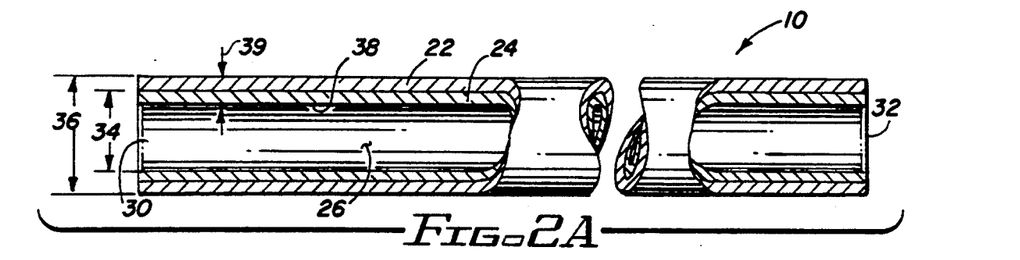
FIG. 2A is a cross-sectional view of an empty coated micropipette, as seen along the line 2—2 in FIG. 1.
Figure 2B:
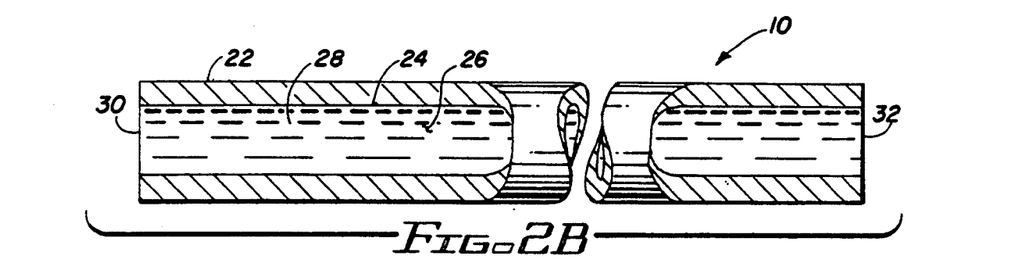
FIG. 2B is a cross-sectional view of the coated micropipette, as seen along the line 2—2 in FIG. 1, filled with a sample solution to be analyzed.
Figures 2C, 3, 4:
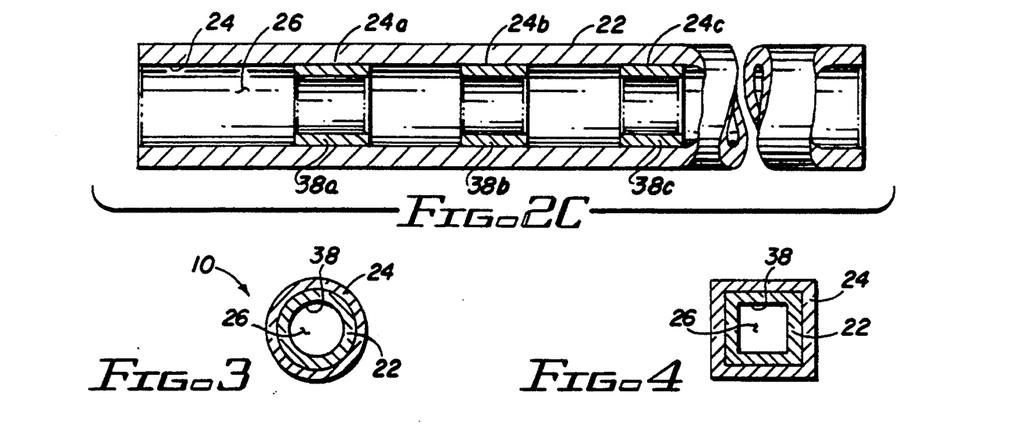
FIG. 2C is a cross-sectional view of an alternative embodiment of an empty coated micropipette, showing multiple reagents, as would be seen along the line 2—2 in FIG. 1.
FIG. 3 is a cross-sectional view of the coated micropipette, as seen along the line 3—3 in FIG. 1.
FIG. 4 is a cross-sectional view of an alternate embodiment of the coated micropipette, as would be seen along the line 3—3 in FIG. 1.

The details of micropipette 10 are shown in FIGS. 2A and 3. FIGS. 2A and 3 which depict the micropipette 10 is preferably an elongated, hollow, transparent capillary micropipette that has a cylindrical outer wall 22 and a cylindrical inner wall 24. It is to be understood that while inner wall 24 and outer wall 22 are cylindrical in shape, that inner wall 24 or outer wall 22, or both, may have other suitable shapes. For example, as shown with reference to FIG. 4, micropipette 10 may have a square cross-section and wall 24 and wall 22 may be shaped as elongated parallelepipeds.

For either embodiment of the micropipette 10, that is for both the square and the circular cross section, inner wall 24 defines a lumen 26 in which a sample solution 28 (shown in FIG. 2B) may be held for analysis. Micropipette 10 is also formed with open ends 30, 32 and while micropipette 10 may be any suitable capillary tube, in the preferred embodiment micropipette 10 is a capillary tube which has an inner diameter 34 of approximately fifty five hundredths (0.55 mm) of a millimeter and an outer diameter 36 of approximately seventy hundredths (0.7 mm) of a millimeter.

FIG. 2A also shows that inner wall 24 of micropipette 10 is coated with a coating composition 38 and, preferably, has a thickness 39 of approximately five (5) to fifty (50) microns ($\mu$). The coating composition 38 contains one or more reagents that react with compounds present in the sample solution. In FIG. 2B, micropipette 10 is shown after it has been filled with the sample solution 28. Upon introduction of the sample solution, all or a portion of the reagent in the coating composition 38 dissolves in the solution. Thus, FIG. 2B shows that reagent has dissolved in the sample solution. More particularly, the reagent (shown in FIG. 2A) combines with compounds in the sample solution 28 (shown in FIG. 2B) to form a solution which has particular light interaction characteristics, that is, particular light absorption or light emission characteristics.

Accordingly, it will be recognized by the skilled artisan that the reagent that is selected is a function of the expected composition of the sample solution 28. For example, if the sample solution 28 is analyzed to detect or measure the concentration of deoxyribonucleic acid (DNA) molecules, then the reagent should be one, such as a Hoechst dye or ethidium bromide, that enhances detection of DNA. Ethidium bromide and the Hoechst dye, as is well known, interact with DNA molecules in solution to form complexes that have known fluorescent characteristics. Alternatively, the reagent may be a material which reacts with compounds in the sample solution 28 to form a solution that has particular light absorption characteristics. In either case, the light emission or light absorption characteristics, as appropriate, can be measured using spectrometer 14 in accordance with well-known principles to detect, identify or measure the concentration of a compound in the sample solution 28. It may, in certain instances, be possible to rely on visual observation of the color change in the sample solution to detect or identify the compound in solution and to estimate its concentration in the solution.

Finally, FIG. 2C shows that multiple reagents can be deposited on predetermined portions of inner wall 24. More particularly, multiple pads of coating containing different reagents 38a, 38b, 38c can be deposited on predetermined portions 24a, 24b, 24c or inner wall 24 by any of the below-disclosed techniques to respectively react with several compounds present in the sample solution. The reagent "pads" 38a, 38b, 38c can even be "chemstix" pads which can be introduced within lumen 26 to respectively adhere to portions 24a, 24b, 24c of inner wall 24.

Preparation of the coating composition.

The coating composition is prepared by mixing a reagent for spectroscopically detecting a compound in a sample solution with a suitable solvent, such as water, to form a coating mixture, which, when deposited and evaporated onto the walls forms a coating composition. The concentration of the reagent in the composition must be sufficient to quantitatively bind to all of the particular compound, for which it is specific, in the sample solution and to uniformly, longitudinally and azimuthally, coat the tube. In addition, the concentration of reagent must be uniform after it has dissolved in the sample solution. The coating cannot dissolve immediately upon contact with the solution because of the time it takes to fill the tube.

In preferred embodiments, the tube and the coating composition, including the reagent, are selected from ingredients that can be deposited on the inner surface of the tube such that the reagent is reversibly bound to the wall. In embodiments, described below in which multiple reagents are deposited in annular "pads", the tubes, coating composition and reagent are selected from ingredients and materials that result in irreversibly or substantially irreversible binding of the reagent or reagents to the wall.

The reagent may be any compound known to those of skill in the art for use in spectroscopic assays. Such reagents include, but are not limited to, Lowry reagent which binds to proteins to produce complexes that absorb at 700-750 nm (Lowry et al. (1951) *J. Biol. Chem.* 193: 265); Biuret $CU^{2+}$, which forms complexes to proteins that absorb at 540 nm (Gornall et al. (1949) *J. Biol. Chem.* 177: 751); dyes such as Coomassie brilliant blue G250, which binds to protein in acid solutions (Bradford (1976) *Anal. Biochem.* 116: 53); Hoechst 33258 (2-(2-(4-hydroxyphenol)-6-benzymidazoyl-6(1-methyl-4-piperazyl)benzimidazole), which interacts with DNA and increases its fluorescence (Labarca et al. (1979) *Anal. Biochem.* 102: 344); fluorescamine, which is a heterocyclic dione that reacts with primary amines to form a fluorescent product (Udenfried et al. (1972) *Science* 176: 871); ethidium bromide and ethidium homodimer, which exhibit enhanced fluorescence in presence of DNA or RNA (Karsten et al. (1972) *Anal. Biochem.* 77: 464); and other reagents such as enzymes that interact chemically with a compound of interest to produce chemiluminescence, bioluminescence or a spectroscopically detectable product. For example, bacterial luciferase and firefly luciferase react with a substrate in the sample solution and produce bioluminescence. Firefly luciferase is used to measure ATP and bacterial luciferase is use to measure NADPH.

The concentration of reagent in the coating composition is sufficient to react with all of the molecules in the sample solution for which it is specific, but is not added in large excess, which result in low signal to noise ratio. Preferably about twenty times the desired concentration of the reagent in the sample solution is added to the coating composition. For example, in order to achieve a final concentration of a dye, such as Hoechst dye, that is sufficient to quantitatively detect DNA in the range of about 10–100 μg, about 20 ng dye per centimeter length of capillary is added to the coating composition.

In order to delay or retard immediate dissolution of the reagent in the sample solution, a binder or adhesive is included in the coating composition or is coated onto the surface of the tubes prior to deposition of the coating composition. The binder is a compound or mixture of compounds, such as sucrose, polysaccharides, polyacrylamide, agarose, and other gels, that delays dissolution of the reagent into the sample solution and that does not appreciably or substantially interact with the sample solution. The binding reagent acts as a time release agent with respect to the coating reagent by delaying immediate dissolution of the reagent by at least about 5 to 15 seconds. The binding agent is preferably a mixture of simple sugars, polysaccharides, or gelatin. The preferred binding agent is prepared by mixing sucrose in water. The binding agent may be used to pre-coat the tubes, or the reagent and any other components of the coating composition may be mixed with the binding agent and then coated on the walls of the tubes.

To prepare binding agents, candidate compounds, such as sugar, gelatins, are polysaccharides, are mixed at various concentrations, from about 0–1600 gm/liter, mixed with a selected reagent and introduced into a tube. The coating is then tested to see if the selected agents retard or delays dissolution of the coating in water or other appropriate solvent. Concentrations and mixtures that delay dissolution by at least about 5 to 15 seconds are selected. Generally, concentrations of such binder of on the order of about 5 gm/liter of gelatin, 1600 gm/liter of sucrose or mixtures of various concentrations of sucrose and gelatin in the coating composition are effective. One of skill in the art may readily test mixtures of other suitable binders and other concentrations to ascertain the optimal composition for use with a particular reagent and sample type.

Since the coating on the inside of the capillaries may interfere with or alter normal capillary action, it is generally necessary to use means, other than capillary action to introduce sample solution into the tubes.

Deposition of the coating composition onto the inner walls of the tube.

In preferred embodiments, the coating mixture is deposited onto the walls of the tube resulting in a uniform coating in which the reagent is reversibly bound to the wall.

In preferred embodiments the coating is introduced into the tube using a thin needle, such as a syringe needle, under pressure, such as that exerted by a syringe or a precision pump. When introducing the coating into the tube, care should be taken to ensure that the fluid air interface moves at a constant rate down the tube.

After the coating solution is introduced into the tube, it is removed. It may be removed by suction or by pressure. If suction, such as that exerted by a syringe is used, the needle should be filled with fluid prior to withdrawing the fluid from the capillary.

Figure 5:
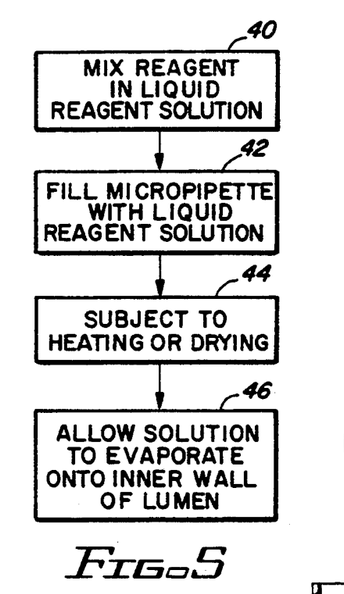
FIG. 5 is a block diagram of one method of depositing the reagent within the coated micropipette.
Figure 6:
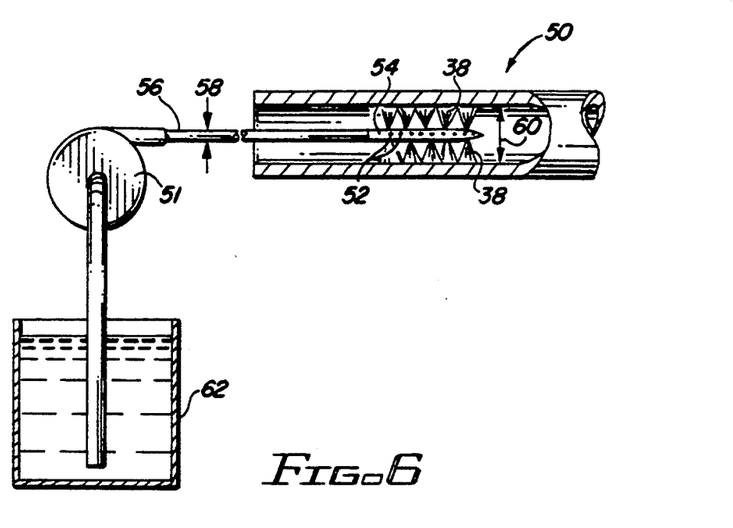
FIG. 6 is a schematic diagram of an alternate method of depositing the reagent within the coated micropipette, with the micropipette shown in cross-section for clarity.
Figure 7:
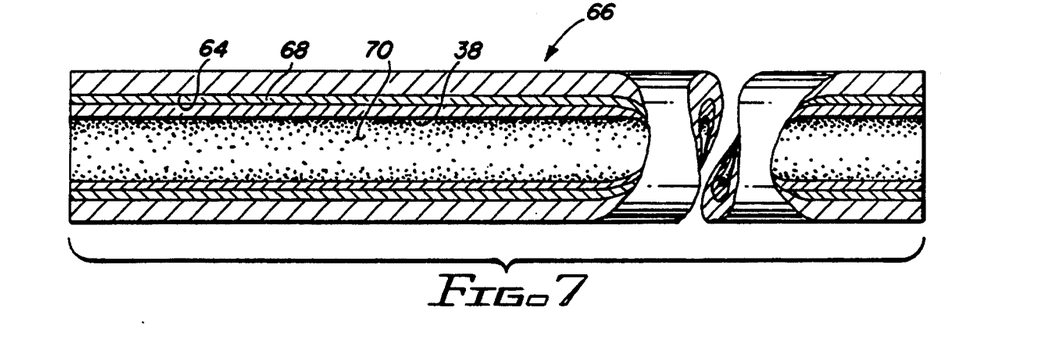
FIG. 7 is a cross-sectional view of an alternate embodiment of the coated micropipette, as would be seen along the line 2—2 in FIG. 1, showing an adhesive layer deposited within the micropipette.

Other embodiments are depicted in the Figures. FIGS. 5, 6, and 7 show non-limiting alternative methods for depositing the coating solution containing the reagent 38 onto the inner wall 24 of micropipette 10.

FIG. 5, depicts a method in block diagram in which reagent is mixed with a suitable solvent, for example water, to form a liquid coating mixture. This step is represented at block 40. Then, the coating mixture is drawn into either of the open ends 30, 32 of micropipette 10, as indicated at block 42, by applying a partial vacuum to the opposite open end of micropipette 10, by injecting the composition into the micropipette or by the capillary action of micropipette 10. The lumen 26 of micropipette 10 can be filled with the liquid coating solution.

Next, micropipette 10 is subjected to drying or evaporating conditions including, but not limited to, vacuum drying or heating to a temperature sufficient, generally room temperature up to and including about 37°–38° C., as indicated at block 44, in order to evaporate the liquid reagent solution, as indicated at block 46. No heat or vacuum is needed if the deposition solution will evaporate at room temperature. As the coating mixture containing the reagent solution evaporates out of open ends 30 and 32, the coating composition containing the reagent 38 is deposited on inner wall 24 as a residue in which the reagent or reagents, except in instances when multiple annular "pads" are intended to be deposited, are reversibly bound to the inner wall.

FIG. 6 shows that coating composition containing the reagent 38 may alternatively be deposited onto the inner wall 48 of a micropipette 50 by spraying. More specifically, the coating composition mixture including the reagent 38 is sprayed through holes 52 of a nozzle 54 of a spraying hose 56. To this end, diameter 58 of hose 56 is smaller than inner diameter 60 of micropipette 50. Consequently, nozzle 54 and portions of hose 56 can be positioned inside micropipette 50 for spraying the coating mixture onto the inner wall 48. To these ends, apparatus 56 is hollow and the lumen of apparatus 56 is in fluid communication with a source 62 of the coating mixture containing the reagent 38. Source 62 may be an enclosed reservoir that can be pressurized by air (not shown). Alternatively, source 62 can be acted upon by a pump 51 (shown schematically in FIG. 6) to force the coating mixture containing the reagent 38 through hose 56 and out of holes 52 of nozzle 54. As the coating mixture containing the reagent 38, which has been sprayed onto the wall 48, evaporates, a uniform layer of the coating composition is deposited onto wall 48. The method shown in FIG. 6 is particularly useful when the inside diameter 60 of micropipette 50 is too large to establish the capillary action necessary to hold an infused liquid within micropipette 50 or when the coating mixture is too viscous for capillary action to be effective.

Finally, FIG. 7 shows that an inner wall 64 of a micropipette 66 can be covered with an adhesive coating 68. Adhesive coating 68 may be infused into micropipette 66 to adhere to inner wall 64, or may be sprayed onto inner wall 64. Then, the coating mixture containing reagent 38 in dry powdered, granulated or liquid form can be introduced by any suitable means into the lumen 70 of micropipette 66. Portions of the coating mixture containing the reagent 38 will adhere to coating 68. Any excess that does not adhere to coating 68 may then be blown, drawn out, or evaporated from lumen 70. Importantly, coating 68 is preferably an inert material which will not interact, for analysis purposes, with sample solutions that are introduced into micropipette 66 for analysis.

Finally, FIG. 2C shows that multiple reagent "pads" 38a, 38b, 38c can be deposited on inner wall 24 to respectively react with several compounds in the sample solution 28. Each of the respective reagent-substance 28 complexes can be analyzed using the techniques discussed above to determine the composition of the sample solution 28 in which the reagent dissolves in the solution.

Introduction of sample solution into the coated tubes and use thereof for spectroscopic analysis of the sample solution.

In describing the method of use of micropipette 10, reference is made to FIGS. 1, 2A, and 2B. The inner wall 24 of micropipette 10 is initially coated with reagent 38, as shown in FIG. 2A. Then, a sample solution 28 is introduced into lumen 26 of micropipette 10. At least a portion of the reagent in the coating composition dissolves in the sample solution and interacts in some manner, including by chemical or physical interactions, with compounds in solution 28 to form a complex that has particular light absorption or light emission characteristics that differ from unbound reagent and compound. It is to be understood that for purposes herein, the reagent in the coating composition 38 forms a complex with selected compounds in the solution 28 and that the electromagnetic interaction characteristics of the resulting solution are analyzed to detect, identify or quantify compounds in the solution to which the reagent binds. For example, if the reagent is a dye, a transparent micropipette 10 can be visually observed to determine what, if any, color changes the solution 28 exhibits upon interaction of certain compounds in the solution 28 combining with the reagent within lumen 26. Observed color changes can be correlated in accordance with well-known principles to the concentration of the compound in the sample solution 28.

On the other hand, more precise determination of the composition of the sample 28 is possible using spectroscopy rather than simple visual inspection of micropipette 10. If it is desirable to make a relatively precise determination of the concentration of compounds in sample solution 28, micropipette 10 is filled with sample solution 28 and then placed within adapter 12 in the path of light from light source 16. For the particular application, in which the reagent is fluorescent or results in fluorescent solution when it binds with a compound in the sample solution 28, the spectrometer which includes source 16 and detector 18 is a fluorescence spectrometer. The sample solution fluoresces as the light from source 16 interacts with the molecules of the solution. This fluorescence is received by detector 18 and subsequently correlated with the concentration of a particular compound in the sample solution 28 by well known principles of spectroscopy. Alternatively, certain compounds in the sample solution 28 may interact with particular reagents to produce complexes or other products that have distinct light absorption characteristics and are, therefore, more appropriately analyzed using spectrophotometry. In these instances, micropipette 10 is placed in an absorbance spectrophotometer and the sample solution analyzed using well-known spectrophotometric principles.

The following example is included for illustrative purposes only and are not intended to limit the scope of the invention.

EXAMPLE

The composition used for coating the capillary tube was prepared by mixing 25 ml of water and 40 grams of sucrose. Hoechst dye, designated H33258, was added to the mixture to yield a final concentration of about 100 $\mu$g/ml. The capillary tubes were placed in a holding rig and the above composition was introduced into the tubes. A syringe was used to fill the capillary tubes leaving about 4 mm empty at one end of the tube. The empty end of the tubes were positioned near a second syringe with a hypodermic needle, which had been pre-filled with the coating solution. The needle was inserted into the tube to fill empty space in the tube and the syringe was attached to a vacuum system. Negative pressure, about $-50$ to about $-100$ mm Hg, was applied to withdraw the excess coating solution from the tube. Air was then drawn through the tube for about a minute to dry the coating onto the inside of capillary.

After the coating has dried, the capillary tubes may be stored for future use, or a sample solution containing DNA or RNA may be introduced into a capillary for spectrometric analysis. The sample solution is introduced into the coated capillary by any suitable means, and a sufficient amount to quantitatively measure the concentration of DNA or RNA dissolves, after a 5 to 15 sec. delay, in the sample solution.

While the particular coated tube as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Since modifications will be apparent to those of skill in the art, it is intended that this invention be limited only by the scope of the appended claims.

What is claimed:

1. A container, which is constructed so as to be mounted in a spectrometer and which is used for detecting the presence of or quantifying the amount of a biopolymer or biopolymers in a sample solution that is introduced into the container, comprising:

a micropipette or capillary tube that is transparent to at least a portion of the electromagnetic spectrum emitted and detected by a spectrometer and that is constructed so as to be mounted in the spectrometer whereby light passes through the walls of said tube; and a coating composition deposited on the inner wall of said tube, wherein:

the coating contains one or more reagents and a binding agent;

wherein the binding agent delays distribution of the reagent in the sample solution for at least about 5 seconds to permit uniform dissolution upon filling, and which said binding agent contains one or more ingredients selected from the group consisting of a sugar, a polysaccharide, a gelatin, a polyacrylamide, and agarose, the reagent specifically interacts with one or more biopolymers in the sample solution to form complexes, whereby, upon exposure to electromagnetic radiation emitted by the spectrometer through the walls of the tube, the complexes absorb or emit electromagnetic radiation; and the coating contains a sufficient amount of the reagent(s) in the coating to permit detection of the complexes by the spectrometer.

2. The container of claim 1, wherein the reagent is a molecule which specifically interacts with a biopolymer selected from the group consisting of DNA and RNA to form a complex that absorbs, emits or produces electromagnetic radiation of a particular wavelength to detect, identify, and quantitate the concentration of the biopolymer.

3. The container of claim 1, wherein the binding agent is sucrose, gelatin or a mixture of sucrose and gelatin.

4. The container of claim 1, wherein said binding agent is deposited on said wall between said reagent and said wall.

5. The container of claim 1, wherein said binding agent and reagent are mixed prior to deposition on said wall.

6. A method for analyzing a sample solution, comprising:
   introducing the solution into a container of claim 1;
   directing incident electromagnetic radiation into the container; and
   detecting electromagnetic radiation that is transmitted from or through the container, wherein the container is transparent to both the incident and transmitted electromagnetic radiation.

7. The method of claim 6, wherein the reagent is a molecule which specifically interacts with a biopolymer selected from the group consisting of DNA and RNA to form a complex that absorbs, emits or produces electromagnetic radiation of a particular wavelength to detect, identify, and quantitate the concentration of the biopolymer.

8. A method for uniformly coating a reagent and a binding agent onto the inner wall of a capillary tube which is constructed so as to be mounted in a spectrometer and can be used for quantifying the amount of a biopolymer or biopolymers in a sample solution that is introduced into the capillary tube, because the reagent will specifically interact with one or more biopolymers in the sample solution to form complexes, which complexes upon exposure to electromagnetic radiation emitted by the spectrometer through the walls of the tube, absorb or emit electromagnetic radiation,
   which method comprises:
   introducing a coating mixture in the form of a solution that includes a binding agent and at least one reagent into one end of the tube;
   drawing said coating mixture through the tube by applying a partial vacuum to the opposite end and removing excess coating mixture therethrough; and
   subjecting the container to evaporating conditions to evaporate and remove the solvent whereby a uniform coating composition of said reagent attached by said binding agent is formed on the inner wall of the capillary tube.

9. The method of claim 8, wherein removal of said solvent is effected by the flow of air by applying suction or pressure.

10. The method of claim 8, wherein the outside diameter of said capillary tube is not greater than about 0.7 mm.

11. A container, which is constructed so as to be mounted in a spectrometer and which is used for detecting the presence of or quantifying the amount of a biopolymer or biopolymers in a sample solution that is introduced into the container, comprising:
   a micropipette or capillary tube that is transparent to at least a portion of the electromagnetic spectrum emitted and detected by a spectrometer and that is constructed so as to be mounted in the spectrometer whereby light passes through the walls of said tube; and
   a coating composition deposited on the inner walls of said tube, wherein:
   the coating contains a plurality of reagents that specifically interact with one or more compounds in the sample solution to form complexes that emit or absorb electromagnetic radiation; and
   each reagent is deposited in a discrete and separate location on the wall and remains bound to the wall upon introduction of the sample solution.

* * * * *